US009000210B2

(12) United States Patent
Kreis et al.

(10) Patent No.: US 9,000,210 B2
(45) Date of Patent: Apr. 7, 2015

(54) PREPARATION OF SUBSTITUTED 2-FLUOROACRYLIC ACID DERIVATIVES

(75) Inventors: Michael Kreis, Leverkusen (DE); Jan Kirchhoff, Düsseldorf (DE)

(73) Assignee: Saltigo GmbH, Leverkusen (DE)

( * ) Notice: Subject to any disclaimer, the term of this patent is extended or adjusted under 35 U.S.C. 154(b) by 190 days.

(21) Appl. No.: 13/379,062

(22) PCT Filed: Jun. 23, 2010

(86) PCT No.: PCT/EP2010/058870
§ 371 (c)(1),
(2), (4) Date: Jul. 30, 2012

(87) PCT Pub. No.: WO2010/149683
PCT Pub. Date: Dec. 29, 2010

(65) Prior Publication Data
US 2012/0283468 A1    Nov. 8, 2012

(30) Foreign Application Priority Data
Jun. 26, 2009   (DE) .................. 10 2009 030 681

(51) Int. Cl.
*C07C 67/317*    (2006.01)
*C07C 67/307*    (2006.01)

(52) U.S. Cl.
CPC ............. *C07C 67/307* (2013.01); *C07C 67/317* (2013.01)

(58) Field of Classification Search
CPC .................................................. C07C 67/317
See application file for complete search history.

(56) References Cited

U.S. PATENT DOCUMENTS 2,245,547 A * 6/1941 Pollack ..................... 560/213
5,124,476 A    6/1992 Gassen et al.

FOREIGN PATENT DOCUMENTS

JP        60078943 A  *  5/1985
JP       2001172223 A     6/2001

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Belokon et al, Amino Acids, Asymmetric Synthesis of Enantiomerically and Diastereoisomerically Enriched 4-[F or Br]-substituted Glutamic Acids, 2010,. 39, pp. 1171-1176.*
Elkik et al, Bulletin Societe Chemique de France, 1979, pp. 65-70.*
International Search Report dated Sep. 28, 2010 for PCT/EP2010/058870, 2 pages.
Gassen et al., "Synthese von α-Fluoracrylsäure und Derivaten", Journal of Fluorine Chemistry (Dec. 1991), 55(2):149-162.
Tolman et al., "Synthesis of 2-Fluoropropenoic Acid Derivatives", Collect. Czech. Chem. Commun. (1983), vol. 48(1):319-326.
Elkik et al, Bull. Soc. Chem. Fr. (1975), pp. 1633-1638.
Elkik et al., "Preparation of 3-amino-2-fluoropropionic and 2-fluoroacrylic esters", C.R. Acad. Sc. Paris, Series C (Jun. 28, 1976), 282(24)1129-1131.
Elkik et al., "Fluoroalkylation of β-dicarbonyl derivatives. Preparation of 4-fluorocyclohexane-1, 3-diones", Bull. Soc. Chem. Fr. (1979), 1-2, Pt. 2:65-70.
Muslinkin et al., "Synthesis of Some α-Fluoracryl Esters", Russian Journal of Applied Chemistry (Jan. 1, 2009), 82(1):116-122.

* cited by examiner

*Primary Examiner* — Paul A Zucker
(74) *Attorney, Agent, or Firm* — Jennifer R. Seng

(57) ABSTRACT

The present invention relates to a process for the preparation of substituted 2-fluoroacrylic acid derivatives.

14 Claims, No Drawings

PREPARATION OF SUBSTITUTED 2-FLUOROACRYLIC ACID DERIVATIVES

The present invention relates to a process for the preparation of substituted 2-fluoroacrylic acid derivatives.

Substituted 2-fluoroacrylic acid derivatives are starting materials in the synthesis of polymers. These can, e.g., be used as plastics in optical waveguides and as polymeric additives in medicaments.

Various processes for the preparation of substituted 2-fluoroacrylic acid derivatives are known from the literature.

Journal of Fluorine Chemistry, 55, 1991, pp. 149-162, reveals a process for the preparation of substituted 2-fluoroacrylic acid derivatives, in particular 2-fluoroacrylic acid esters, by hydrolysis of α-hydroxymethyl-α-fluoromalonic acid esters, subsequent decarboxylation and renewed esterification. The process exhibits the disadvantage that only low yields are obtained.

An additional process is known from JP 2001172223 AA, in which it is described that substituted 2-fluoroacrylic acid derivatives can be prepared from 2,2-bromofluoropropionic acid esters. This process has the disadvantage that the starting materials are not readily available, the process is accordingly unusable economically and only low yields are obtained.

EP 0415214 A1 gives a description of a four-stage process for the preparation of a substituted 2-fluoroacrylic acid derivatives, namely the 2-fluoroarcrylic acid ester, starting from 2,3-dichloro-1-propene. Additional processes for the preparation of substituted 2-fluoroacrylic acid derivatives starting from 3-hydroxy-2-fluoropropionates, by reaction with toluenesulfonyl chloride and removal of the tosylate formed in the presence of potassium phthalimide, are known from Journal of Fluorine Chemistry, 1993, 60, pp. 149-162, and from Coll. Czech. Chem. Commun., 1983, 48, pp. 319-326. These processes have in common the fact that they cannot be used in industrial processes for economic and safety reasons.

An additional process for the preparation of substituted 2-fluoroacrylic acid derivatives by reaction of 3-hydroxy-2-fluoropropionates with dehydrating agents is known from Bull. Soc. Chem. Fr., 1975, pp. 1633-1638. This process likewise has the disadvantage of low reaction yields.

It is common to all processes that either they are unsuitable for safety and economic reasons or they give excessively low reaction yields.

There accordingly furthermore continued to exist a need for a process for the preparation of substituted 2-fluoroacrylic acid derivatives which overcomes the disadvantages of the state of the art and by which substituted 2-fluoroacrylic acid derivatives can be efficiently prepared in industrial processes.

Surprisingly, a process for the preparation of substituted 2-fluoroacrylic acid derivatives has been found in which substituted 3-halo-2-fluoropropionic acid derivatives are converted, in the presence of bases, to substituted 2-fluoroarylic acid derivatives with good yields and high purities.

A subject-matter of the invention is accordingly a process for the preparation of compounds of the formula (I):

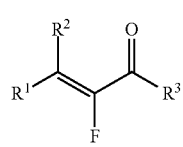

(I)

in which $R^1$ and $R^2$ are identical or different and are, independently of one another, hydrogen, $C_1$-$C_{15}$-alkyl, $C_6$-$C_{24}$-aryl, $C_1$-$C_{15}$-alkoxy, $C_2$-$C_{10}$-alkenyl, $C_6$-$C_{24}$-aryloxy, $C_7$-$C_{15}$-arylalkyl, $C_1$-$C_{15}$-alkylthio, $C_1$-$C_{15}$-mono- and dialkylamino, $C_6$-$C_{24}$-mono- and diarylamino or 5- to 8-membered saturated or unsaturated heterocyclyl, which optionally in addition can be substituted by radicals chosen from the group consisting of $C_1$-$C_{15}$-alkyl, $C_2$-$C_{10}$-alkenyl, $C_1$-$C_{15}$-alkoxy, $C_6$-$C_{24}$-aryl, $C_7$-$C_{15}$-arylalkyl, $C_1$-$C_{15}$-alkylthio, halo, hydroxyl, cyano, nitro, amino, carboxyl, $C_1$-$C_{15}$-haloalkyl, $C_2$-$C_{10}$-haloalkenyl, $C_1$-$C_{15}$-haloalkoxy, $C_1$-$C_{15}$-haloalkylthio and 5- to 8-membered saturated or unsaturated heterocyclyl, or $R^1$ and $R^2$ together form a carbocyclic or heterocyclic and saturated or unsaturated 4- to 8-membered ring which optionally in addition can be substituted by radicals chosen from the group consisting of $C_1$-$C_{15}$-alkyl, $C_2$-$C_{10}$-alkenyl, $C_1$-$C_{15}$-alkoxy, $C_6$-$C_{24}$-aryl, $C_7$-$C_{15}$-arylalkyl, $C_1$-$C_{15}$-alkylthio, halo, hydroxyl, cyano, nitro, amino, carboxyl, $C_1$-$C_{15}$-haloalkyl, $C_2$-$C_{10}$-haloalkenyl, $C_1$-$C_{15}$-haloalkoxy, $C_1$-$C_{15}$-haloalkylthio and 5- to 8-membered saturated or unsaturated heterocyclyl, and $R^3$ is $C_1$-$C_{15}$-alkoxy, $C_1$-$C_{15}$-mono- and dialkylamino, $C_6$-$C_{24}$-aryloxy, $C_6$-$C_{24}$-mono- and diarylamino and 5- to 8-membered saturated or unsaturated heterocyclyl which is connected via a heteroatom, which optionally in addition can be substituted by radicals chosen from the group consisting of $C_1$-$C_{15}$-alkyl, $C_2$-$C_{10}$-alkenyl, $C_1$-$C_{15}$-alkoxy, $C_1$-$C_{15}$-alkylthio, $C_6$-$C_{24}$-aryl, $C_7$-$C_{15}$-arylalkyl, halo, hydroxyl, cyano, nitro, amino, carboxyl, $C_1$-$C_{15}$-haloalkyl, $C_2$-$C_{10}$-haloalkenyl, $C_1$-$C_{15}$-haloalkoxy, $C_1$-$C_{15}$-haloalkylthio and 5- to 8-membered saturated or unsaturated heterocyclyl, in which compounds of the formula (II):

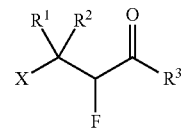

(II)

in which $R^1$, $R^2$ and $R^3$ have the abovementioned meanings and X is Cl, Br, I or a pseudohalogen, are reacted in the presence of at least one base and in the presence of at least one polymerization inhibitor to give compounds of the formula (I).

In a preferred embodiment, $R^1$ and $R^2$ are, independently of one another, can be identical or different and are preferably hydrogen, $C_1$-$C_6$-alkyl, $C_6$-$C_{24}$-aryl, $C_1$-$C_6$-alkoxy, $C_2$-$C_6$-alkenyl, $C_6$-$C_{24}$-aryloxy, $C_7$-$C_{10}$-arylalkyl, $C_1$-$C_6$-alkylthio, $C_1$-$C_8$-mono- and dialkylamino, $C_6$-$C_{24}$-mono- and diarylamino or 5- to 8-membered saturated or unsaturated heterocyclyl, which optionally in addition can be substituted by radicals chosen from the group consisting of $C_1$-$C_6$-alkyl, $C_2$-$C_6$-alkenyl, $C_1$-$C_6$-alkoxy, $C_6$-$C_{24}$-aryl, $C_7$-$C_{15}$-arylalkyl, $C_1$-$C_6$-alkylthio, amino, halo, cyano, carboxyl, hydroxyl, nitro, $C_1$-$C_6$-haloalkyl, $C_2$-$C_6$-haloalkenyl, $C_1$-$C_6$-haloalkoxy, $C_1$-$C_6$-haloalkylthio and 5- to 8-membered saturated and unsaturated heterocyclyl, or $R^1$ and $R^2$ together form a carbocyclic or heterocyclic and saturated or unsaturated 4- to 8-membered ring, which optionally in addition can be substituted by radicals chosen from the group consisting of hydroxyl, cyano, nitro, amino, carboxyl, $C_1$-$C_6$-alkyl or $C_6$-$C_{24}$-aryl. $R^1$ and/or $R^2$ are particularly preferably $C_1$-$C_6$-alkyl, $C_1$-$C_6$-alkoxy, $C_6$-$C_{24}$-aryl or hydrogen. $R^1$ and/or $R^2$ are very particularly preferably methyl, ethyl, propyl, isopropyl, n-butyl, isobutyl, s-butyl, t-butyl, n-pentyl, phenyl or hydrogen.

$R^3$ is preferably $C_1$-$C_6$-alkoxy, $C_1$-$C_8$-mono- and dialkylamino, $C_1$-$C_6$-alkylthio, $C_6$-$C_{24}$-aryloxy, $C_6$-$C_{24}$-mono- and diarylamino or 5- to 8-membered saturated or unsaturated heterocyclyl which is connected via a nitrogen atom, which optionally in addition can be substituted by radicals chosen from the group consisting of $C_1$-$C_6$-alkyl, $C_2$-$C_6$-alkenyl, $C_1$-$C_6$-alkoxy, $C_6$-$C_{24}$-aryl, $C_7$-$C_{15}$-arylalkyl, $C_1$-$C_6$-alkylthio, amino, halo, cyano, carboxyl, hydroxyl, nitro, $C_1$-$C_6$-haloalkyl, $C_2$-$C_6$-haloalkenyl, $C_1$-$C_6$-haloalkoxy and $C_1$-$C_6$-haloalkylthio. $R^3$ is particularly preferably methoxy, ethoxy, n-propoxy, isopropoxy, t-butoxy, n-pentoxy, n-hexoxy, cyclopropoxy, cyclobutoxy, cyclopentoxy, cyclohexoxy, cycloheptoxy, ethylamino, diethylamino, methylamino, dimethylamino, butylamino, dibutylamino, propylamino, dipropylamino, benzylamino, phenoxy, pyrrolidinyl, piperazinyl or pyridazinyl. Methoxy, ethoxy, propoxy, methylamino, ethylamino, pyrrolidinyl, piperazinyl or pyridazinyl are very particularly preferred.

X is preferably Cl or Br. X is particularly preferably chlorine.

The context of the invention encompasses all definitions of radicals, parameters and explanations cited above and below, mentioned in general terms or in preferred ranges, in any combination with one another, i.e. also between the respective ranges and preferred ranges.

Alkyl or alkoxy or alkylthio is, in the context of the invention, a straight-chain, cyclic or branched alkyl or alkoxy or alkylthio radical with from 1 to 15 ($C_1$-$C_{15}$), preferably from 1 to 12 ($C_1$-$C_{12}$) and particularly preferably from 1 to 6 ($C_1$-$C_6$). By way of example, alkyl is methyl, ethyl, n-propyl, isopropyl, n-butyl, isobutyl, s-butyl, t-butyl, cyclopropyl, cyclobutyl, cyclopentyl, cyclohexyl, cycloheptyl, n-pentyl, 1-methylbutyl, 2-methylbutyl, 3-methylbutyl, neopentyl, 1-ethylpropyl, n-hexyl, n-heptyl, n-octyl, n-decyl and n-dodecyl. Preferably, alkyl is methyl, ethyl, n-propyl, isopropyl, n-butyl, isobutyl, s-butyl, t-butyl, cyclopropyl, cyclobutyl, cyclopentyl, n-hexyl, cyclohexyl, n-pentyl, 1-methylbutyl, 2-methylbutyl, 3-methylbutyl, neopentyl, 1-ethylpropyl and cyclohexyl. Particularly preferably, alkyl is methyl, ethyl, n-propyl, isopropyl, n-butyl, isobutyl, s-butyl, t-butyl, n-pentyl and n-hexyl. By way of example and preferably, alkoxy is methoxy, ethoxy, n-propoxy, isopropoxy, n-butoxy, isobutoxy, s-butoxy, t-butoxy, n-pentoxy, n-hexoxy, cyclopropoxy, cyclobutoxy, cyclopentoxy, cyclohexoxy or cycloheptoxy. By way of example and preferably, alkylthio is methanethio, ethanethio, n-propanethio, isopropanethio, n-butanethio, isobutanethio, s-butanethio, t-butanethio, n-pentanethio, 1-methylbutanethio, 2-methylbutanethio, 3-methylbutanethio, neopentanethio, 1-ethylpropanethio and n-hexanethio.

Alkenyl is, in the context of the invention, a straight-chain, cyclic or branched alkenyl radical with from 2 to 10 ($C_2$-$C_{10}$), preferably with from 2 to 6 ($C_2$-$C_6$) carbon atoms. By way of example and preferably, alkenyl is vinyl, allyl, isopropenyl and n-but-2-en-1-yl.

Aryl is, in the context of the invention, an aromatic radical with from 6 to 24 backbone carbon atoms, in which no, one, two or three backbone carbon atoms per ring, in the entire molecule however at least one backbone carbon atom, can be replaced by heteroatoms chosen from the group consisting of nitrogen, sulfur or oxygen; however, aryl is preferably an aromatic carbocyclic radical with from 6 to 24 backbone carbon atoms. The same applies for the aromatic part of an arylalkyl radical. Furthermore, the aromatic carbocyclic or heteroaromatic radicals can be substituted with up to five identical or different substituents per ring chosen from the group consisting of $C_1$-$C_6$-alkyl, $C_2$-$C_6$-alkenyl, $C_1$-$C_6$-alkoxy, amino, $C_7$-$C_{15}$-arylalkyl, carboxyl, $C_1$-$C_8$-mono- and dialkylamino, halo, nitro, cyano, carboxyl, $C_1$-$C_6$-haloalkyl, $C_1$-$C_6$-haloalkenyl, $C_1$-$C_6$-haloalkoxy, $C_1$-$C_6$-haloalkylthio and hydroxyl.

Preferred examples of $C_6$-$C_{24}$-aryl are phenyl, o-, p- or m-tolyl, naphthyl, phenanthrenyl, anthracenyl or fluorenyl. Examples of heteroaromatic $C_6$-$C_{24}$-aryl in which one, two or three backbone carbon atoms per ring, in the entire molecule however at least one backbone carbon atom, can be replaced by heteroatoms chosen from the group consisting of nitrogen, sulphur and oxygen are pyridyl, pyrimidyl, ppidazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl, benzofuranyl or dibenzofuranyl.

Arylalkyl is, in each case independently of one another, a straight-chain, cyclic or branched alkyl radical according to the above definition which can be substituted once, several times or completely by aryl radicals according to the above definition. An example of arylalkyl is benzyl. Preference is given to arylalkyls with from 7 to 15 ($C_7$-$C_{15}$) carbon atoms; particular preference is given to arylalkyls with from 7 to 10 ($C_7$-$C_{10}$) carbon atoms.

Aryloxy is, in the context of the invention, a $C_6$-$C_{24}$-aryl radical of the above definition which is connected via an oxygen atom. By way of example, the aryl radical can be further substituted by radicals chosen from the group consisting of $C_1$-$C_6$-alkyl, $C_2$-$C_6$-alkenyl, $C_1$-$C_6$-alkoxy, amino, $C_7$-$C_{15}$-arylalkyl, carboxyl, $C_1$-$C_8$-mono- and dialkylamino, halo, nitro, cyano, carboxyl, $C_1$-$C_6$-haloalkyl, $C_1$-$C_6$-haloalkenyl, $C_1$-$C_6$-haloalkoxy, $C_1$-$C_6$-haloalkylthio and hydroxyl. By way of example and preferably, aryloxy is phenoxy.

Mono- and diarylamino is, in the context of the invention, an amino group which is bonded to one or two identical or different $C_6$-$C_{24}$-aryl radicals of the above definition and is connected via the nitrogen atom. By way of example, the aryl radical can be additionally substituted by radicals chosen from the group consisting of $C_1$-$C_6$-alkyl, $C_2$-$C_6$-alkenyl, $C_1$-$C_6$-alkoxy, amino, $C_7$-$C_{15}$-arylalkyl, carboxyl, $C_1$-$C_8$-mono- and dialkylamino, halo, nitro, cyano, carboxyl, $C_1$-$C_6$-haloalkyl, $C_1$-$C_6$-haloalkenyl, $C_1$-$C_6$-haloalkoxy, $C_1$-$C_6$-haloalkylthio and hydroxyl.

In the context of the invention, 5- to 8-membered saturated or unsaturated heterocyclyl is preferably a saturated or unsaturated heterocycle radical, with up to 3 identical or different heteroatoms from the series S, N and/or O, which is connected via a ring carbon atom, ring nitrogen atom, ring oxygen atom or ring sulfur atom. By way of example, the 5- to 8-membered saturated or unsaturated heterocyclyl can be further substituted by radicals chosen from the group consisting of $C_1$-$C_6$-alkyl, $C_2$-$C_6$-alkenyl, $C_1$-$C_6$-alkoxy, amino, $C_7$-$C_{15}$-arylalkyl, carboxyl, $C_1$-$C_8$-mono- and dialkylamino, halo, nitro, cyano, carboxyl, $C_1$-$C_6$-haloalkyl, $C_1$-$C_6$-haloalkenyl, $C_1$-$C_6$-haloalkoxy, $C_1$-$C_6$-haloalkylthio and hydroxyl. Preference is given to a 5- to 8-membered saturated heterocyclyl with up to 2 identical or different heteroatoms from the series S, N and/or O. By way of example and preferably, mention may be made of azepanyl, pyrrolidinyl, piperidinyl, piperazinyl, morpholinyl or tetrahydrofuryl.

Monoalkylamino or dialkylamino is, in the context of the invention, an amino group which is bonded to one or two identical or different and cyclic, noncyclic, straight-chain or branched alkyl substituents which preferably exhibit(s) in each case from 1 to 15 carbon atoms. Particularly preferably, the amino group is bonded to one or two identical or different and cyclic, noncyclic, straight-chain or branched alkyl substituents which preferably exhibit(s) from 1 to 12 carbon atoms, very particularly preferably exhibit(s) from 1 to 8 carbon atoms. By way of example, the alkyl radical can be additionally substituted by radicals chosen from the group consisting of $C_1$-$C_6$-alkyl, $C_2$-$C_6$-alkenyl, $C_1$-$C_6$-alkoxy, amino, $C_7$-$C_{15}$-arylalkyl, carboxyl, $C_1$-$C_8$-mono- and dialkylamino, halo, nitro, cyano, carboxyl, $C_1$-$C_6$-haloalkyl, $C_1$-$C_6$-haloalkenyl, $C_1$-$C_6$-haloalkoxy, $C_1$-$C_6$-haloalkylthio and hydroxyl.

By way of example and preferably, monoalkylamino is methylamino, ethylarnino, n-propylamino, isopropylamino, t-butylamino, n-pentylamino and n-hexylamino.

By way of example and preferably, dialkylamino is N,N-dimethylarnino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Haloalkyl or haloalkenyl or haloalkoxy is, in the context of the invention, a straight-chain, cyclic or branched alkyl or alkenyl or alkoxy radical according to the above definition which is substituted once, several times or completely by halogen atoms.

By way of example and preferably, $C_1$-$C_{15}$-haloalkyl is dichloromethyl, difluoromethyl, fluoromethyl, trifluoromethyl, trichloromethyl, 2,2,2-trifluoroethyl, trifluoromethyl, pentafluoroethyl, heptafluoropropyl, nonafluorocyclopentyl, nonachlorocyclopentyl, heptafluoroisopropyl and nonafluorobutyl.

By way of example and preferably, $C_2$-$C_6$-haloalkenyl is chloroethylene, dichloroethylene or trifluoroethylene.

By way of example and preferably, $C_1$-$C_6$-haloalkoxy is difluoromethoxy, fluoroethoxy, fluoromethoxy, trifluoromethoxy, trichloromethoxy and 2,2,2-trifluoroethoxy.

Haloalkylthio is, in the context of the invention, a straight-chain, cyclic or branched radical with from 1 to 15 carbon atoms, preferably with from 1 to 6 ($C_1$-$C_6$) carbon atoms, which is substituted once, several times or completely by halogen atoms. By way of example and preferably, $C_1$-$C_{15}$-haloalkylthio is chloroethylthio, chlorobutylthio, chlorohexylthio, chloropentylthio, chlorododecylthio, dichloroethylthio, fluoroethylthio, trifluoromethylthio and 2,2,2-trifluoroethylthio.

Halogen is fluorine, chlorine, bromine or iodine. Pseudohalogen can, by way of example and preferably, be cyanide, cyanate or thiocyanate.

Bases within the meaning of the invention are, e.g., alkaline earth or alkali metal hydroxides, atnides, alkoxides, carbonates, hydrogenphosphates, or phosphates, such as, for example, sodamide, lithium diethylamide, sodium methoxide, potassium tert-butoxide, sodium hydroxide, potassium hydroxide sodium carbonate, potassium carbonate, sodium phosphate, potassium phosphate, sodium hydrogenphosphate or potassium hydrogenphosphate, and also tertiary amines, such as trimethylamine, triethylamine, tributylamine, diisopropylethylamine, tripentylamine, trihexylamine, trioctylamine, N,N-dimethylaniline, piperidine, N-methylpiperidine, N,N-dimethylaminopyridine and also imidazole, 1,4-diazabicyclo[2.2.2]octane (DABCO), 1,5-diazabicyclo[4.3.0]non-5-ene (DBN), 1,8-diazabicyclo[5.4.0]undec-7-ene (DBU), 1,1,3,3-tetramethylguanidine (TMG), 7-methyl-1,5,7-triazabicyclo[4.4.0]dec-5-ene (MTBD) and 2,8,9-triisopropyl-2,5,8,9-tetraaza-1-phosphabicyclo[3.3.3]undecane (TTPU) or mixtures of these bases. Preference is given to the use of bi- or tricyclic bases, trialkylamines or inorganic carbonates, hydrogencarbonates, hydroxides, hydrogenphosphates or phosphates. Particular preference is given to the use of 1,4-diazabicyclo[2.2.2]octane (DABCO), 1,5-diazabicyclo[4.3.0]non-5-ene (DBN), 1,8-diazabicyclo[5.4.0]undec-7-ene (DBU), 1,1,3,3-tetramethylguanidine (TMG), 7-methyl-1,5,7-triazabicyclo[4.4.0]dec-5-ene (MTBD), 2,8,9-triisopropyl-2,5,8,9-tetraaza-1-phosphabicyclo[3.3.3]undecane (TTPU), triethylamine, trimethylamine, tributylamine, trihexylamine, trioctylamine, imidazole, dipotassium hydrogenphosphate, potassium phosphate, disodium hydrogenphosphate, sodium phosphate, potassium carbonate, sodium carbonate, sodium hydroxide, potassium hydroxide or mixtures of these bases. Very particularly preferably, use is made, as base, of 1,4-diazabicyclo[2.2.2]octane (DABCO), 1,5-diazabicyclo[4.3.0]non-5-ene (DBN), 1,8-diazabicyclo[5.4.0]undec-7-ene (DBU), triethylamine, trimethylamine, tributylamine, sodium carbonate, potassium carbonate, sodium phosphate or potassium phosphate.

The process according to the invention can, for example, be carried out in the presence or in the absence of a solvent. The process according to the invention is preferably carried out in the presence of a solvent.

Use may be made, as solvent in the process according to the invention, by way of example and preferably, of polar aprotic solvents, such as sulfoxides, such as, e.g., dimethyl sulfoxide, such as ethers, such as, e.g., polyethylene glycols, ethylene glycol dimethyl ether, ethylene glycol diethyl ether, ethylene glycol dibutyl ether, diethylene glycol dimethyl ether, tetraethylene glycol dimethyl ether, dioxane, tetrahydrofuran or 1,2-dimethoxyethane, such as sulfones, such as, e.g., sulfolane (tetramethylsulfone), such as amide solvents, such as, e.g., dimethylformamide, N-methylpyrrolidone, N-methylcaprolactam or dimethylacetamide, such as ketones, such as, e.g., dipropyl ketone or methyl tert-butyl ketone, or nitriles, such as, e.g., benzonitrile or benzyl nitrile, or halogenated aromatic compounds, such as, e.g., chlorobenzene or ortho-dichlorobenzene, or mixtures of such solvents. Use is preferably made, as polar aprotic solvents, of polyethylene glycols, ethylene glycol dimethyl ether, ethylene glycol diethyl ether, ethylene glycol dibutyl ether, diethylene glycol dimethyl ether, tetraethylene glycol dimethyl ether, dimethylfoimamide, dimethyl sulfoxide, sulfolane, ortho-dichlorobenzene or N-methylpyrrolidone, or mixtures of such solvents. The process according to the invention is particularly preferably carried out in the presence of a high-boiling-point solvent. In the context of the invention, a solvent is then regarded as a high-boiling-point solvent if the boiling point of the solvent at a pressure of 1 bar is ≥140° C. Use is very particularly preferably made, as high-boiling-point polar aprotic solvent, of ethylene glycol dibutyl ether, diethylene glycol dimethyl ether, tetraethylene glycol dimethyl ether, dimethylformamide, dimethyl sulfoxide, sulfolane, ortho-dichlorobenzene or N-methylpyrrolidone, or mixtures of such solvents.

Use may be made, as polymerization inhibitor, by way of example and preferably, of free nitroxyl radicals, such as, for example, 2,2,6,6-tetramethylpiperidine N-oxyl, sulfur, p-benzoquinone, 4-tert-butylcatechol, phenothiazine, di-tert-butylhydroxytoluene (BHT) or sterically hindered phenols, or mixtures of these polymerization inhibitors. Use is preferably made of di-tert-butylhydroxyltoluene (BHT).

The process according to the invention is preferably carried out at a temperature of 50° C. to 200° C., particularly preferably at 70 to 180° C. and very particularly preferably at 130° C. to 170° C.

The molar ratio of the polymerization inhibitor to the compounds of the formula (II) used is, for example, between $1*10^{-6}$ and $1*10^{-1}$, preferably between $5*10^{-6}$ and $5*10^{-3}$ and particularly preferably between $1*10^{-5}$ and $1*10^{-3}$.

The molar ratio of the compounds of the formula (II) used to the base used is, for example, between 0.1 and 10, preferably between 0.3 and 2 and particularly preferably between 0.5 and 1.5.

In the process according to the invention, the polymerization inhibitor, solvent and base are, for example, introduced first. By way of example, the mixture can then be heated to the reaction temperature and a vacuum can be applied. By way of example, the addition of the compounds of the formula (II) can then be begun. Likewise, by way of example as well, only the base and the solvent might first be added and the polymerization inhibitor might be mixed with the compounds of the formula (II) and, for example, only then might be added. The addition of the reaction components and mixtures takes place, e.g. in metered fashion. The compounds of the formula (I) can, for example, be separated continuously in the process according to the invention, e.g. by distillation.

The process according to the invention is preferably carried out so that the polymerization inhibitor, the solvent and the base are first introduced and the mixture is heated to the reaction temperature. Preferably, a vacuum is then applied and the compounds of the formula (II) are added. Preferably, the compounds of the formula (I) produced are separated during the reaction. Preferably, this takes place by distillation.

Many of the compounds in the process according to the invention are commercially available or can be prepared by analogous processes known from the state of the art which are known to a person skilled in the art.

It is certainly preferred to prepare the compounds of the formula (II) from compounds of the formula (III), in which the compounds of the formula (III):

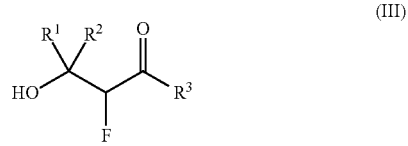

(III)

in which $R^1$, $R^2$ and $R^3$ exhibit the meanings mentioned for the compounds of the formula (I),
are reacted
optionally in the presence of at least one solvent and
optionally in the presence of at least one base
with halogenating agents to give compounds of the formula (II).

Use may be made, as halogenating agent for the preparation of the compounds of the formula (II), by way of example and preferably, of thionyl chloride, thionyl bromide, phosphorus trichloride, phosphorus tribromide, sulfuryl chloride, sulfuryl bromide or HX with X=Cl, Br or F, or mixtures of these compounds. Use is particularly preferably made of thionyl chloride.

The process for the preparation of the compounds of the formula (II) is preferably carried out in the presence of at least one inert solvent. Preferred solvents in the process for the preparation of the compounds of the formula (II) are inert nonpolar aliphatic or aromatic solvents, such as, for example, benzene toluene, xylene, various petroleum ethers, hexane, cyclohexane, optionally halogenated hydrocarbons, such as, e.g., carbon tetrachloride, or mixtures of such organic solvents. Particularly preferred are benzene, hexane, petroleum ethers, toluene, p-xylene and xylene isomer mixture, or mixtures of such solvents.

Moreover, the preparation of the compounds of the formula (II) from the compounds of the formula (III) is preferably carried out in the presence of a base. In this case, use is preferably made, as bases, of alkaline earth or alkali metal hydroxides, alkoxides, carbonates, hydrogenphosphates or phosphates, such as, for example potassium tert-butoxide, sodium hydroxide, potassium hydroxide, sodium carbonate, potassium carbonate, sodium phosphate, potassium phosphate, sodium hydrogenphosphate or potassium hydrogenphosphate, and also tertiary amines, such as trimethylamine, triethylamine, tributylamine, diisopropylethylamine, N,N-dimethylaniline, piperidine, pyridine, N-methylpiperidine, N,N-dimethylaminopyridine and also 1,4-diazabicyclo[2.2.2]octane (DABCO), 1,5-diazabicyclo[4.3.0]non-5-ene (DBN), 1,8-diazabicyclo[5.4.0]undec-7-ene (DBU), 1,1,3,3-tetramethylguanidine (TMG), 7-methyl-1,5,7-triazabicyclo[4.4.0]dec-5-ene (MTBD) and 2,8,9-triisopropyl-2,5,8,9-tetraaza-1-phosphabicyclo[3.3.3]undecane (TTPU), or mixtures of these bases. Use is particularly preferred of bi- or tricyclic bases, pyridine, N-methylpiperidine, N,N-dimethylaminopyridine or piperidine, or mixtures of these bases.

The process for the preparation of the compounds of the formula (II) from compounds of the formula (III) is preferably carried out at a temperature of from 0° C. to 25° C., particularly preferably at from 0° C. to 5° C.

The molar ratio of the halogenating agents to the compounds of the formula (III) is, for example, between 0.8 and 1.5 and preferably between 1.0 and 1.5.

The preparation of the compounds of the formula (II) from the compounds of the formula (III) is preferably carried out under essentially anhydrous conditions. Under essentially anhydrous conditions means that the water content, based on the amounts of the reaction mixture used, is preferably between 0.0001% by weight and 1.0% by weight.

The process for the preparation of the compounds of the formula (II) from the compounds of the formula (III) is, for example, carried out so that first the base and the solvent are introduced. This mixture can, for example, first be heated to from 30 to 100° C. The mixture is preferably heated to from 60 to 90° C. The formation of unwanted secondary components can be markedly reduced by addition of a temperature of 30° C. to 100° C. By way of example, the halogenating agents and the compounds of the formula (III) are mixed in a separate container. The mixture of the halogenating agents and of the compounds of the formula (III) can then be added to the mixture of base and solvent. By way of example, however, the halogenating agents and the compounds of the formula (III) can likewise first be mixed and introduced. By way of example, the mixture of base and solvent can then first be heated and then, by way of example, be added at a temperature of from 30° C. to 100° C. By way of example, the addition of the reaction components and mixtures is carried out in metered fashion.

The process for the preparation of the compounds of the formula (II) from the compounds of the formula (III) is first preferably carried out so that the base and the solvent are introduced. This mixture is then preferably heated to from 60° C. to 90° C. Preferably, the halogenating agent is introduced into another container and the compounds of the formula (III) are added. This mixture is preferably added in metered fashion to the mixture of base and solvent.

The compounds of the formula (III) are commercially available or can be prepared by analogous processes known from the state of the art which are known to a person skilled in the art.

The formation of unwanted secondary products can be reduced using the process for the preparation of the compounds of the formula (II) from the compounds of the formula (III). Moreover, with the process, compounds of the formula (III) are prepared in good yields even with the use of small amounts of halogenating agents and at low temperatures.

The purification of the compounds of the formula (II) and also of the compounds of the formula (I) can be carried out according to processes known to a person skilled in the art, for example by extraction with solvents, distillation or crystallization.

The compounds of the formula (I) can be prepared, by the process according to the invention, in high yields and in high purity in an industrially simple way. The process for the invention does not require the handling of chemicals which, because of their hazard potential, require specialist expenditure and it can be carried out without problems even on a relatively large scale. It is in particular surprising that the process according to the invention produces the compounds of the formula (I) in high yields and in high purity.

The compounds of the formula (I) prepared according to the invention are suitable in particular for the preparation of plastics and polymeric additives in medicaments.

The following examples serve to clarify the invention without in this connection being limited thereto.

EXAMPLES

1. Preparation of methyl 3-chloro-2-fluoropropionate

An amount of thionyl chloride of 743 g (6.3 mol) is introduced into a sulfonation pan and cooled to 5° C. An amount of methyl 3-hydroxy-2-fluoropropionate of 748 g (98%, 6.)0 mol) is metered in at 5±5° C. in accordance with the evolution of gas. After complete addition, the mixture is subsequently stirred at 0° C. to 30° C. An amount of pyridine of 24 g (0.30 mol) and 332 g of toluene are introduced into a second sulfonation pan, the mixture is heated to 80° C. and the chlorination mixture from sulfonation pan 1 is metered herein in accordance with the evolution of gas. After complete addition, the mixture is subsequently stirred at 80° C. Subsequently, first toluene is distilled off under reduced pressure (200-500 mbar) via a packed column, followed by the fractional distillation of the product at 20 mbar (boiling point: 70° C.). An amount of product of 742 g (5.28 mol, 88% yield) is obtained as colorless liquid.

2. Preparation of methyl 2-fluoroacrylate

An amount of di-tert-butylhydroxytoluene (BHT) of 4 g (0.02 mol), 500 g of N-methylpyrrolidine (NMP) and 360 g (2.2 mol) of tribasic sodium phosphate are introduced into a sulfonation pan and the mixture is heated to 150° C. An amount of di-tert-butylhydroxytoluene (BHT) of 51 mg ($2.2*10^{-4}$ mol) is introduced into the distillation receiver of the vertical recovery bend. A vacuum of 300 mbar is applied and the metered addition of a total of 287 g (98%, 2.0 mol) of methyl 3-chloro-2-fluoropropionate is begun. The metered addition is continued in the degree in which the methyl 2-fluoroacrylate is distilled over. When no more distillate stream passes over, the vacuum is lowered to 150 mbar. When no more product passes over even here, the pressure is raised by addition of nitrogen. The distillation bottoms are cooled and discharged via the bottom valve. The product is obtained after distillation as a colorless liquid (205 g, 95%, 1.87 mol, 93.5% yield).

3. Preparation of ethyl 3-chloro-2-fluoropropionate

An amount of thionyl chloride of 8.99 g (0.08 mol) was introduced at 20-25° C. into a dry 50 ml round-bottomed flask under a nitrogen atmosphere. Ethyl 3-hydroxy-2-fluoropropionate (10.0 g, 0.07 mol) were subsequently metered in in 1 h and the mixture was subsequently stirred at ambient temperature for a further 2 h. An amount of toluene of 3.98 g (0.04 mol), together with 0.286 g of pyridine (5 mol %), were introduced into a second round-bottomed flask with an Anschutz head and the mixture was heated to 80° C., The mixture from the 1st round-bottomed flask was added dropwise to the preheated solution in 1 h at 75-85° C. Solvents were distilled off under reduced pressure and the residue was subsequently finely distilled at 120° C. and 10 mbar. 4.1 g of distillate were obtained as a colorless liquid.

[1] H NMR (400 MHz, $CDCl_3$): 5.67 (dd; J=44 Hz, 3 Hz; CHH); 5.31 (dd; J=13 Hz, 3 Hz; CHH); 4.30 (q, J=7 Hz, $CH_2$), 1.35 (t, J=7 Hz, $CH_3$)ppm.

4. Preparation of ethyl 2-fluoroacrylate

An amount of N-methylpyrrolidine (NMP) of 10 ml (0. mol) was introduced into a 3-necked round-bottomed flask and mixed with 6.19 g of $K_3PO_4$. The suspension was heated to 150° C. and a vacuum of 300 mbar was applied. Ethyl 3-chloro-2-fluoropropionate (4.1 g, 27 mmol) were metered in and the product was simultaneously distilled off. An amount of ethyl 2-fluoroacrylate of 2.7 g was obtained as a colorless liquid which was contaminated with approximately 15% of NMP. The excess NMP could be removed by means of extraction with water. An amount of product of 1.3 g was obtained as a colorless liquid. (Yield 42%).

$^1$H NMR (400 MHz, $CDCl_3$): 5.14 (ddd; J=48 Hz, 5 Hz, 4 Hz; CHF); 4.32 (qd, J=7 Hz, 1 Hz; $CH_2$), 3.95 (dd, J=4 Hz, 1 Hz, CHCl); 3.90 (dd, J=5 Hz, 3 Hz, CHCl); 1.34 (t, J=7 Hz, $CH_3$) ppm.

What is claimed is:

1. A process for the preparation of compounds of the formula (I),

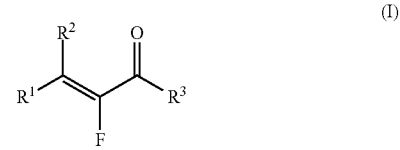

wherein $R^1$ and $R^2$ are identical or different and are, independently of one another, hydrogen, $C_1$-$C_{15}$-alkyl, ($C_6$-$C_{24}$-aryl or $C_1$-$C_{15}$-alkoxy, and $R^3$ is $C_1$-$C_{15}$alkoxy, the process comprising:

reacting compounds of the formula (II),

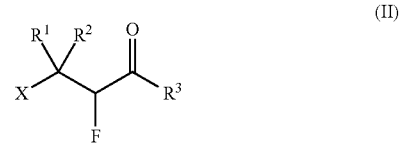

wherein $R^1$, $R^2$ and $R^3$ have the abovementioned meanings, and X is Cl, Br, I or a pseudohalogen, in the presence of:
at least one base,
a high-boiling-point polar aprotic solvent selected from the group consisting of ethylene glycol dibutyl ether, diethylene glycol dimethyl ether, tetraethylene glycol dimethylether, dimethylformamide, dimethyl sulfoxide, sulfolane, ortho-dichlorobenzene, N-methylpyrrolidone, and mixtures thereof, and
at least one polymerization inhibitor selected from the group of 2,2,6,6-tetramethylpiperidine N-oxyl, sulfur, p-benzoquinone, 4-tert-butylcatechol, phenothiazine, di-tert-butylhydroxytoluene (BHT) and mixtures thereof.

2. The process as claimed in claim 1, wherein $R^1$ and/or $R^2$ is hydrogen.

3. The process as claimed in either of claims 1 or 2, wherein $R^3$ is methoxy or ethoxy.

4. The process as claimed in claim 1 wherein the base is 1,4-diazabicyclo[2.2.2]octane (DABCO), 1,5-diazabicyclo[4.3.0]non-5-ene (DBN), 1,8-diazabicyclo[5.4.0]undec-7-ene (DBU), triethylamine, trimethylamine, tributylamine, sodium carbonate, potassium carbonate, sodium phosphate or potassium phosphate, or a mixture of these bases.

5. The process as claimed in claim 1, further comprising carry out the reaction at a temperature of 130° C. to 170° C.

6. The process as claimed in claim 1, wherein the mole ratios of the compounds of the formula (II) to the base are between 0.5 and 1.5.

7. The process as claimed in claim 1, further comprising seperating the compound of the formula (I) from the reaction mixture during the preparation.

8. The process as claimed in claim 1, further comprising preparing the compounds of the formula (II):

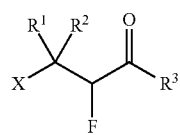

in which $R^1$, $R^2$ and $R^3$ have the meanings listed in claim 1, and X is Cl, Br, I or a pseudohalogen, by reaction of the compounds of the formula (III):

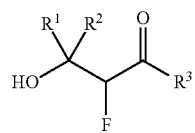

with halogenating agents.

9. The process as claimed in claim 8, wherein the halogenating agent is selected from the group consisting of thionyl chloride, thionyl bromide, phosphorus trichloride, phosphorus tribromide, sulfuryl chloride, sulfuryl bromide, HX with X =Cl, Br or F, or mixtures of these compounds.

10. The process as claimed in claim 1, further comprising carrying out the process in the presence of at least one additional solvent selected from the group consisting of benzene, hexane, petroleum ethers, toluene, p-xylene, xylene isomer mixtures, and mixtures of such solvents.

11. The process as claimed in claim 1, further comprising carrying out the process in the presence of a base selected from the group consisting of bi- or tricyclic bases, pyridine, N-methylpiperidine, N,N-dimethylaminopyridine, piperidine, and mixtures of these bases.

12. The process as claimed in claim 8, wherein the mole ratio of compounds of the formula (III) to the halogenating agents is between 1.0 and 1.5.

13. The process as claimed in claim 1, further comprising heating the mixture of base and solvent to a temperature of 60° C. to 90° C. before or during the addition of the compounds of the formula (III) and/or of the halogenating agents.

14. A process for the preparation of compounds of the formula (I),

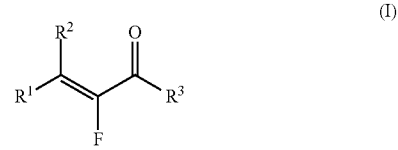

wherein $R^1$ and $R^2$ are identical or different and are, independently of one another, hydrogen, $C_1$-$C_{15}$-alkyl, $C_6$-$C_{24}$-aryl or $C_1$-$C_{15}$-alkoxy, and $R^3$ is $C_1$-$C_{15}$alkoxy, the process comprising:
reacting compounds of the formula (II),

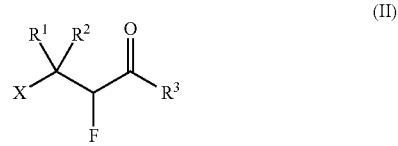

wherein $R^1$, $R^2$ and $R^3$ have the abovementioned meanings, and X is Cl, Br, I or a pseudohalogen, in the presence of:
at least one base,
a high-boiling-point polar aprotic solvent, and
at least one polymerization inhibitor selected from the group of 2,2,6,6-tetramethylpiperidine N-oxyl, sulfur, p-benzoquinone, 4-tert-butylcatechol, phenothiazine, di-tert-butylhydroxytoluene (BHT) and mixtures thereof.

* * * * *